United States Patent [19]

Kendall et al.

[11] Patent Number: 5,279,854

[45] Date of Patent: Jan. 18, 1994

[54] METHOD AND APPARATUS FOR ZONED APPLICATION OF PARTICLES IN FIBROUS MATERIAL

[75] Inventors: Jeffery D. Kendall; Clarence F. Lamber, both of Kent, Wash.

[73] Assignee: Paragon Trade Brands, Inc., Federal Way, Wash.

[21] Appl. No.: 825,928

[22] Filed: Jan. 27, 1992

[51] Int. Cl.$^5$ .................... B05D 1/36; B05C 5/00
[52] U.S. Cl. .................... 427/197; 427/203; 118/308; 118/314; 239/447
[58] Field of Search ............... 427/180, 197, 203, 424, 427/201, 206; 118/308, 314, 325; 604/372, 378; 239/447, 654

[56] References Cited

U.S. PATENT DOCUMENTS

| | | |
|---|---|---|
| 2,577,250 | 12/1951 | Meyer et al. . |
| 3,670,731 | 6/1972 | Harmon . |
| 3,885,066 | 5/1975 | Schwenninger et al. ........... 118/314 |
| 4,087,506 | 5/1978 | Cook et al. . |
| 4,302,481 | 11/1981 | Ribnitz et al. ...................... 427/201 |
| 4,325,988 | 4/1982 | Wagner ............................... 427/180 |
| 4,333,463 | 6/1982 | Holtman . |
| 4,381,783 | 5/1983 | Elias . |
| 4,543,274 | 9/1985 | Mulder . |
| 4,551,191 | 11/1985 | Kock et al. . |
| 4,600,603 | 7/1986 | Mulder . |
| 4,685,915 | 8/1987 | Hasse et al. . |
| 4,699,823 | 10/1987 | Kellenberger et al. . |
| 4,770,344 | 9/1988 | Kaiser . |
| 4,800,102 | 1/1989 | Takada . |
| 4,927,346 | 5/1990 | Kaiser et al. . |
| 4,927,582 | 5/1990 | Bryson . |
| 5,009,650 | 4/1991 | Bernardin . |
| 5,017,324 | 5/1991 | Kaiser et al. . |
| 5,028,224 | 7/1991 | Pieper et al. . |
| 5,056,462 | 10/1991 | Perkins et al. ...................... 118/308 |
| 5,213,817 | 5/1993 | Pelley ................................. 425/81.1 |

FOREIGN PATENT DOCUMENTS 1406615 9/1973 United Kingdom .

OTHER PUBLICATIONS

Applying Chemicals via Spray Technology, David O'Ryan, Nonwovens World, Jun., 1986, pp. 106–112.

Primary Examiner—Terry J. Owens
Attorney, Agent, or Firm—Dressler, Goldsmith, Shore & Milnamow, Ltd.

[57] ABSTRACT

An apparatus and method for forming absorbent articles having superabsorbent particles. Air-entrained absorbent particles are directed through a diverter valve which alternately directs the particles to first and second dispensing nozzles. The nozzles are positioned for dispensing the particles into a moving web of fibrous material, such as wood pulp fluff. Selective operation of the valve in synchronization with the conveying arrangement for the wood pulp fibrous material permits deposition of the absorbent particles in desired patterns within selected portions of the fibrous material.

19 Claims, 3 Drawing Sheets

FIG. I
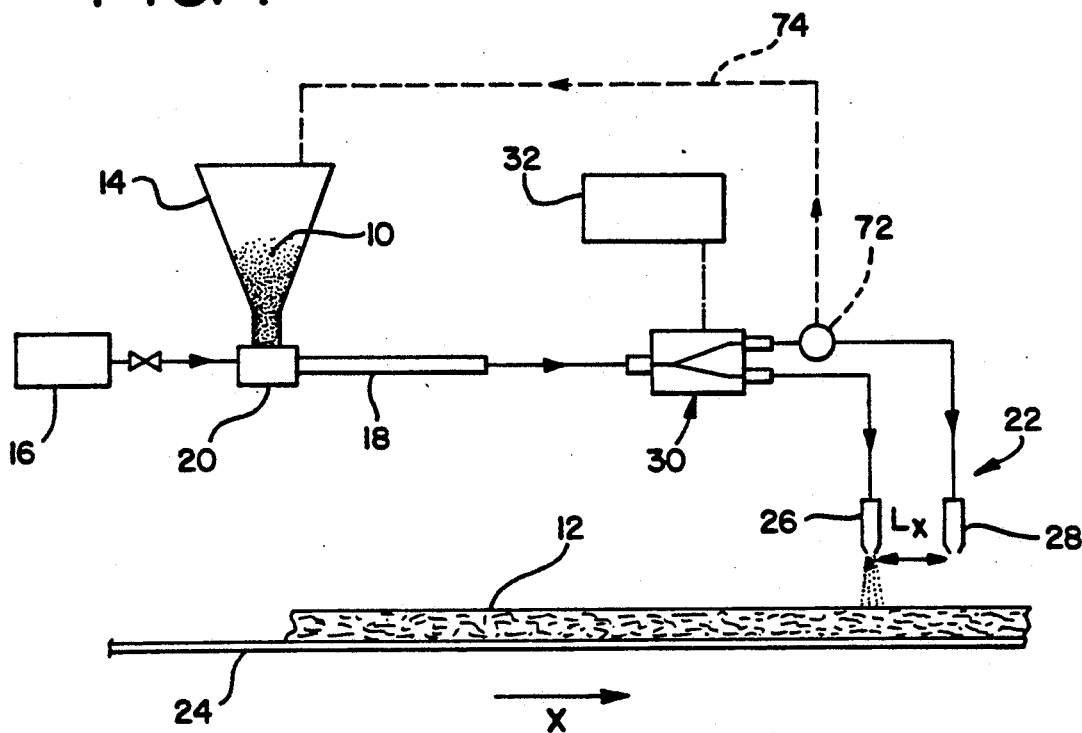
FIG. 4
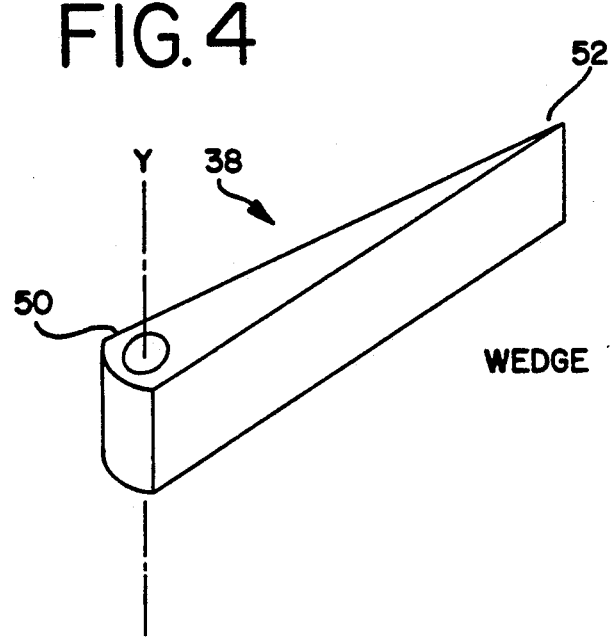
WEDGE

METHOD AND APPARATUS FOR ZONED APPLICATION OF PARTICLES IN FIBROUS MATERIAL

TECHNICAL FIELD

The present invention relates generally to a method and apparatus for zoned application of particles in fibrous material, and more particularly to a method and apparatus for zoned application of superabsorbent polymer particles in an absorbent pad comprising hydrophilic fibrous material such as cellulose fibers.

BACKGROUND OF THE INVENTION

Disposable absorbent articles, such as disposable diapers and the like, usually have an absorbent panel containing superabsorbent polymers to increase the absorbent capacity of the panel while reducing the bulkiness of the article. For example, see U.S. Pat. No. 3,670,731 to Harmon.

Particular absorbent panel constructions contain a zoned region of superabsorbent material in a selected portion of the panel in an attempt to make efficient use of the superabsorbent material. U.S. Pat. No. 4,333,463 to Holtman discloses an absorbent pad which contains a zoned region of superabsorbent material in its front upper or lower portion. U.S. Pat. No. 4,381,783 to Elias describes an absorbent article wherein one or more separate and distinct moisture-permeable cells or pockets containing superabsorbent particles are provided in a crotch region of the article. U.S. Pat. No. 4,685,915 to Hasse et al. suggests application of a zoned deposit of superabsorbent polymers in a central portion of an absorbent article. U.S. Pat. No. 5,009,650 to Bernardin teaches an absorbent structure wherein superabsorbent material is located more at a rearward portion of an absorbent structure.

A number of methods and apparatus have been proposed to manufacture absorbent pad structures having a zoned deposit of superabsorbent material. U.S. Pat. No. 4,087,506 to Cook et al. discloses a method of producing a fluid absorbent web wherein superabsorbent polymer particles are applied onto a central zone of a moving web by means of a spreader. U.S. Pat. No. 4,551,191 to Kock et al. describes an arrangement wherein gas-entrained superabsorbent polymer particles are discharged through a nozzle having a predetermined width in a direction parallel to the direction of travel of the moving porous web so that they are uniformly deposited on the predetermined width portion of the web.

U.S. Pat. No. 4,800,102 to Takada discloses the use of a rotating screen disc having openings of various shapes at intervals, which disc is positioned between a superabsorbent supplier and a moving web so that superabsorbent polymer particles are intermittently deposited on the web at the intervals and patterns corresponding to the openings in the disc. U.S. Pat. Nos. 4,927,346 and 5,017,324 to Kaiser et al. respectively disclose an apparatus and a method for depositing superabsorbent polymer particles into a pad of fibrous material in a forming chamber. A controller selectively directs gas-entrained polymer particles either to a supply hopper or to the fibrous material to produce discrete patterns of superabsorbent polymers along the pad.

U.S. Pat. No. 4,927,582 to Bryson teaches another method for depositing superabsorbent particles into a pad in a forming chamber. The flow velocity of the superabsorbent polymer particles into the forming chamber is controlled so that a selected distribution of the polymer particles is achieved within the fibrous material deposited in the forming chamber. U.S. Pat. No. 5,028,224 to Pieper et al. teaches forming a split stream of superabsorbent material particles by centrifugal segregating means. The split stream is intermittently delivered into a forming chamber so that zoned regions of higher polymer density are formed within the fibrous material.

SUMMARY OF THE INVENTION

The present invention provides a new and improved method and apparatus for zoned application of particles, such as superabsorbent polymer particles, in fibrous material. The present invention contemplates introducing superabsorbent polymer particles into discrete absorbent panel assemblies in discrete in-line zones. The method of application employs a selectively operable diverter valve configured for directing air-fluidized superabsorbent particles through nozzles into a continuous web of fibrous material for subsequent formation of individual absorbent panels.

The superabsorbent polymer particles are fed from a metered powder delivery system into a fluidizing system, which suspends the particles in an air stream (or otherwise gas-entrains the particles) for efficient and controlled application. The metered delivery system operates continuously to feed a predetermined quantity of absorbent particles to each absorbent panel or pad being formed. Once the particles are fluidized, the stream is directed to the entrance of the diverter valve device.

At the diverter valve, the stream of absorbent particles is directed or diverted to either of two nozzle members. The valve may be operated by an electromechanical actuator, or other suitable actuating means, such that the valve is cycled fully between its first and second positions at specific intervals with respect to the absorbent panels of the associated web of fibrous materials. As will be further described, these intervals are timed in the sense that they are dependent upon the position of the associated absorbent panel or pads, and thus are regulated (and thus vary in actual time) depending on surface speed of the fibrous material.

Notably, intervals during which the valve is in each of its first and second positions determines the pattern of absorbent particles to be deposited on the fibrous web. While the ratio or relationship of these intervals can be infinitely varied, they will normally be set such that relatively increased densities of absorbent particles are provided in at least one portion of each individual absorbent pad, with fewer or substantially no particles deposited in other portions of each pad.

As will also be further described, the distance between a pair of dispensing nozzles, through which the absorbent particles are presented to the fibrous web, further determines the pattern of absorbent particles deposited in each absorbent pad. Generalizing, the offset of these two dispensing nozzles corresponds to the offset of each of the first and second deposits of absorbent particles.

An apparatus of the present invention generally includes conveyer means for moving a web of fibrous material in one direction, and nozzle means for discharging gas-entrained absorbent particles into the fibrous material. The conveyor arrangement may take the form of a forming belt operated in conjunction with a vacuum forming chamber, with the nozzle means positioned either within, or outside of, the forming chamber. Alternately, the present invention can be embodied in association with rotary drum-forming devices.

The nozzle means comprises first and second nozzle members spaced from each other in at least the one direction of movement of the fibrous web. Valve means, switchable between two positions, selectively directs the gas-entrained absorbent particles to the first nozzle member in its first position, or to the second nozzle member in its second position.

Control means control the valve means to cause the valve means to switch between the first and second nozzle members at a predetermined interval so that different concentration or density zones of the absorbent particles are formed at selected locations of the fibrous material. In a preferred embodiment of the present invention, the first and second nozzle members are aligned relative to each other along the direction of travel of the fibrous material. In another embodiment of the present invention, one of the first and second nozzle members is replaced with a recirculation line back to the absorbent particle supply system. The recirculation line acts to periodically direct the gas-entrained absorbent particles from the first valve means back to the particle supply means. This action produces intermittent deposit of absorbent particles in the fibrous material with essentially a single pattern or concentration.

The present invention further provides a method for zoned application of absorbent particles in fibrous material. In one aspect of the invention, the method generally comprises the steps of moving fibrous material in one direction, supplying a gas-entrained stream of particles, and selectively directing the gas-entrained particles, at predetermined intervals, to first and second nozzle members which respectively discharge the particles into fibrous material. The method further includes the step of spacing the first and second nozzle members from each other in at least the one direction so that different concentration or density zones of absorbent particles are formed at selected locations of the fibrous material. Again, particle deposition can be effected in conjunction with, or subsequent to, formation of a web of the fibrous material, with eventual formation of individual absorbent panels or pads.

In another aspect of the invention, the method includes the step of selecting the intervals so that the desired combination of first and second deposit patterns of absorbent particles, respectively applied by the first and second nozzle members, is provided in the fibrous material. In particular embodiments, the spaced distance, in the one direction, between the first and second nozzle members determines a length of an overlapped region of the first and second deposit patterns of absorbent particles in the fibrous material, and conversely, an offset of the patterns.

Other features and advantages of the present invention will become readily apparent from the following detailed description, in conjunction with the accompanying drawings, and the appended claims.

BRIEF DESCRIPTION OF THE DRAWINGS

FIG. 1 representatively shows a schematic view of an apparatus embodying the principles of the present invention;

FIG. 4 is a perspective view of a valve vane in accordance with the present invention;

DETAILED DESCRIPTION

Figure 2:
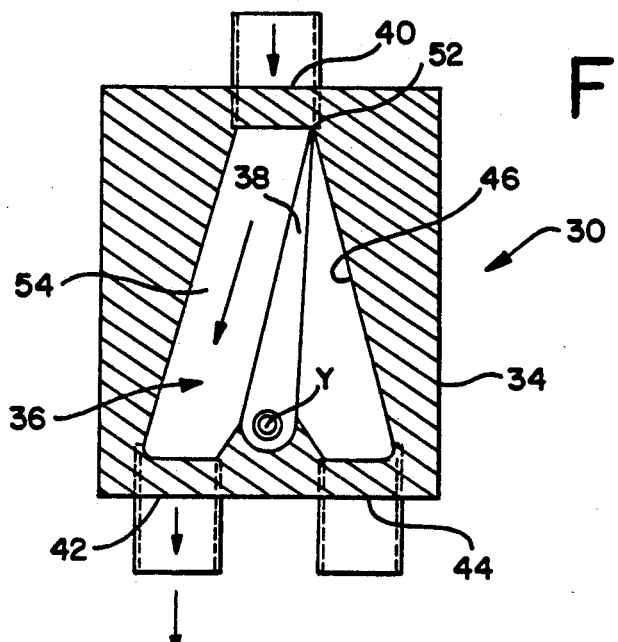
FIG. 2 is a cross-sectional view of valve means of the present invention in its first position.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference now to FIG. 1, therein is illustrated an apparatus for zoned application of absorbent particles, such as superabsorbent polymer particles 10, in fibrous material 12, such as fluff pulp. A delivery system, which generally comprises a particle supply means 14 and a compressed heated-gas supplier 16 (typically supplying pressurized air), provides a gas-entrained (i.e., air-entrained or fluidized) stream of absorbent particles 10. The delivery system further includes a metering means such as a feed auger or the like (not shown) for metering and continuously delivering a predetermined amount of absorbent particles 10.

The particle supply means 14 has a venturi means 20 to which a conduit means 18 is connected. The conduit means 18 supplies the gas-entrained stream of absorbent particles 10 to a nozzle means 22 which discharges absorbent particles 10 into the fibrous material 12 being transported in a direction X by a conveyer means 24. The nozzle means may be positioned within a vacuum forming chamber, in which case the fibrous material is being deposited on the conveyor means with the absorbent particles. Alternately, the nozzle means may deposit the absorbent particles subsequent to formation of the web of fibrous material. Drum forming (i.e., pocket forming) or belt forming equipment may be employed.

The nozzle means 22 has a first nozzle member 26 and a second nozzle member 28 which are spaced from each other a predetermined distance $L_x$ in the moving direction X of the conveyor means 24. A valve means 30 is connected between the conduit means 18 and the nozzle means 22 to regulate communication therebetween. The valve means 30 is selectively switchable between a first position wherein the gas-entrained absorbent particles are directed to the first nozzle member 26, and a second position wherein the gas-entrained absorbent particles are directed to the second nozzle member 28. The valve means 30 is controlled by a control means 32, such as an electromechanical actuator, to cyclically switch between the first and second positions at a predetermined time interval T, typically set by a programmable limit switch means (not shown).

Figure 3:
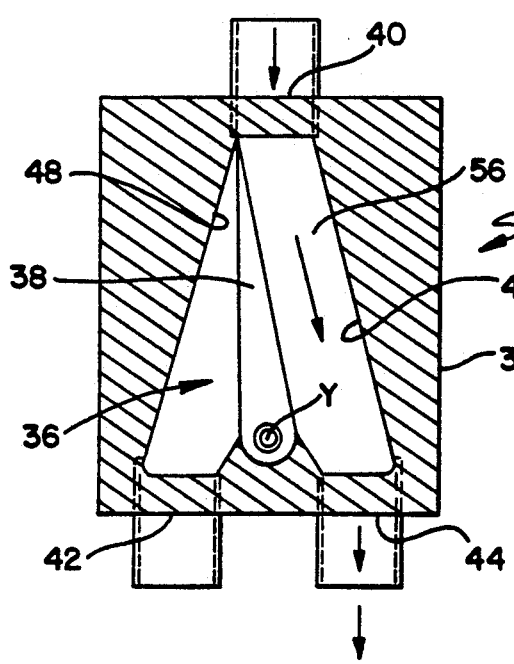
FIG. 3 is a cross-sectional view of valve means in its second position.
Figure 5:
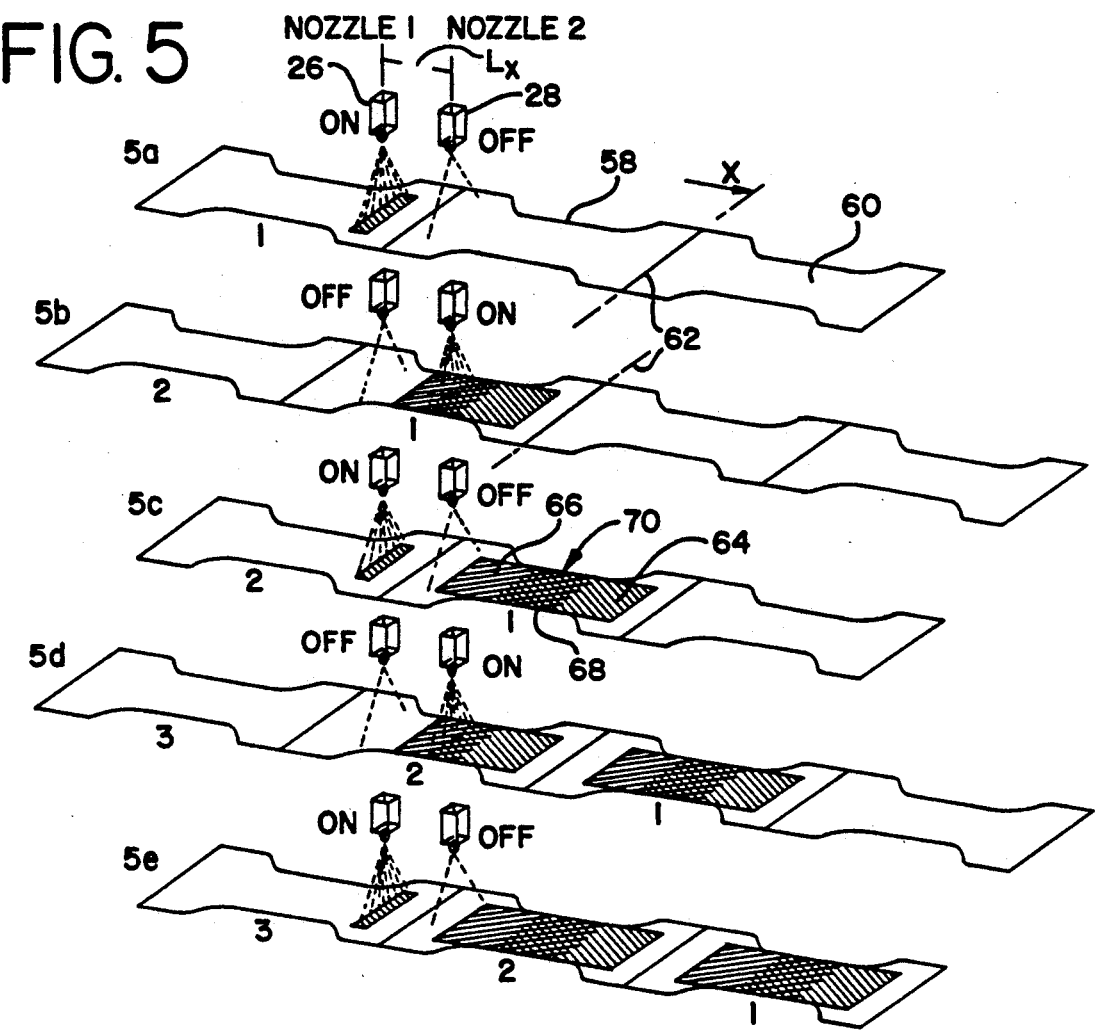
FIGS. 5a, 5b, 5c, 5d, and 5e are schematic perspective views illustrating an exemplified process sequence of forming zoned deposit patterns of absorbent particles in the fibrous material.

In a particular embodiment of the invention, the valve means 30, representatively illustrated in FIGS. 2, 3 and 4, comprises a valve housing 34, a valve chamber 36 and a wedge-like shaped valve vane 38. The valve housing 34 has an inlet port 40 connected in communication with the conduit means 18, and a first outlet port 42 and a second outlet port 44 which are respectively connected in communication with the first nozzle member 26 and the second nozzle member 28. The valve chamber 36 is generally defined between two diverging side walls 46, 48 and forms a generally bifurcated flow passage. The tapered valve vane 38, as best seen in FIG. 4, has a round, wider base end 50 and a generally tranculated tapered edge or an apex 52 extending into the bifurcated flow passage. The valve vane 38 is at its wider base end 50 pivotably mounted intermediate the first and second outlet ports 42, 44 to pivot about an axis Y. The base end 50 at the axis Y is operatively connected to the electromechanical actuator for rotation so that the apex 52 is selectively pressed against one of the side walls 46 when pivoted clockwise, and against another side wall 48 when pivoted counterclockwise, to switch between the first position, as shown in FIG. 2, and the second position, as shown in FIG. 3. In the first position, a linear first flow passage 54 is defined within the valve chamber 36, which joins the inlet port 40 in communication with the first outlet port 42. In the second position, a linear second flow passage 56 is defined within the valve chamber 36, which joins the inlet port 40 in communication with the second outlet port 44. Each of the first and second flow passages 54, 56 has a cross-sectional area which is substantially equal to a cross-sectional area of the inlet port 40 and to a cross-sectional area of its associated outlet port 42 or 44.

Figure 2A:
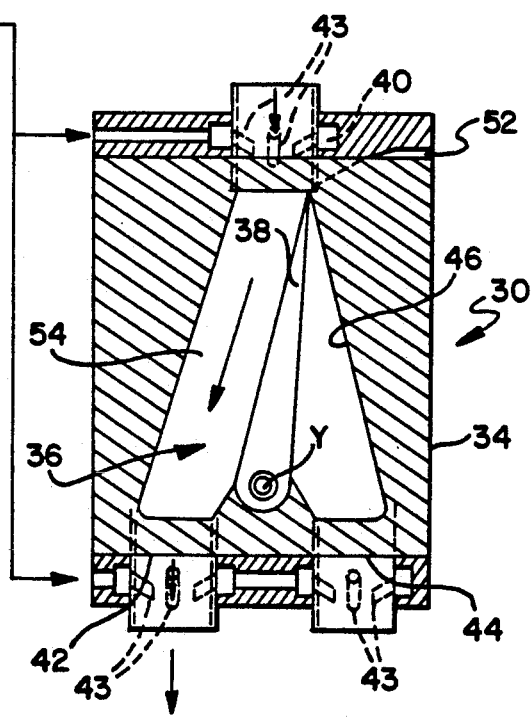
FIG. 2a is a cross-sectional view similar to FIG. 2 illustrating an optional flow augmentation arrangement of the present apparatus.

As illustrated in FIG. 2a, the present apparatus may optionally be provided with means for augmenting the flow of the gas-entrained absorbent particles, thus facilitating fluidized flow from the associated supply arrangement. Such flow augmentation can be effected by providing a plurality of circumferentially spaced angled air inlets 43 generally in the inlet and/or the outlet ports of the valve means 30, which inlets introduce pressurized air supplied thereto from annular passages joined to a source of pressurized air.

Figure 6:
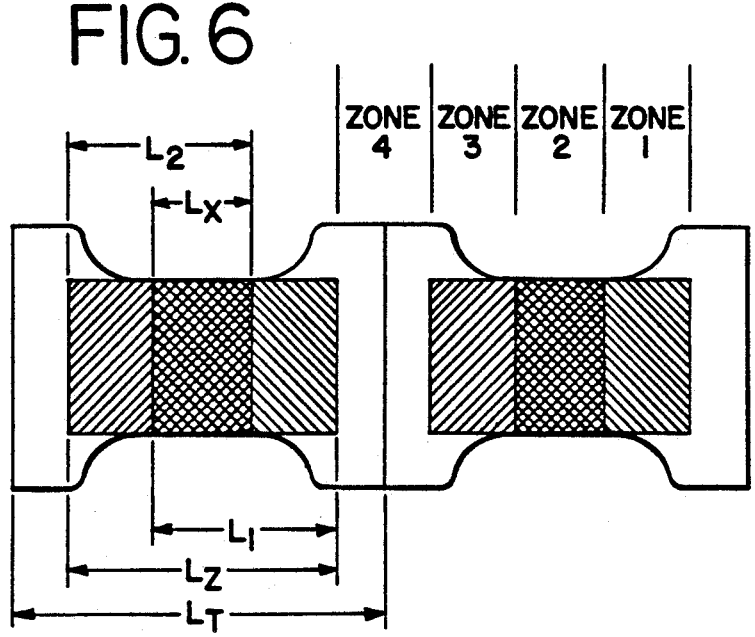
FIG. 6 is a schematic plan view illustrating four distinguished zones of equal length formed in a series of individual absorbent pad units.

Referring to FIGS. 5a through 5e, in conjunction with FIG. 6, one preferred method for zoned application of absorbent particles in an absorbent pad for a disposable diaper is illustrated. A substantially continuous fluff pulp layer 12 is conveyed in the direction X at a predetermined speed. Respective opposite side edges of the layer can be intermittently cut out (either prior or subsequent to particle deposition) for forming leg holes 58 in a series of individual pad units 60 each having a length $L_t$, to later be separated along cut lines 62. The first and second nozzle members 26, 28 are positioned along the direction of movement X of the continuous fluff pulp layer 12 above the layer. Those nozzle members 26, 28 are preferably substantially aligned along a lateral centerline of continuous layer 12 which substantially extends in the direction X, and are spaced from each other a predetermined distance $L_x$.

In the illustrated embodiment of FIGS. 5a through 5e, the valve means 30 is switched to provide equal periods of deposits from the first and second nozzles, with the operation coordinated with the conveyor means 24 so that each nozzle deposits a pattern having a length substantially equal to one-half the length of each absorbent pad unit being formed. Valve means 30 is initially set to its first position which joins conduit means 18 in communication with first nozzle member 26. The delivery system starts operating to supply the gas-entrained stream of absorbent particles 10, through conduit means 18, to first nozzle member 26 as cut line 62 is positioned at in a midpoint between first nozzle member 26 and second nozzle member 28. First nozzle member 26 discharges the gas-entrained absorbent particles 10 onto and into the fluff pulp layer 12 being conveyed during a first time interval $T_1$ to provide in fluff pulp layer 12 a first deposit pattern 64 of absorbent particles 10 having a length $L_1$ and a first density $D_1$ ($g/m^2$).

Valve means 30 is switched to its second position during the subsequent second time interval $T_2$ when second nozzle member 28 discharges the gas-entrained absorbent particles 10 to provide in fluff pulp layer 12 a second deposit pattern 66 of absorbent particles 10 having a length $L_2$ and a second density $D_2$. Valve means 30 is again switched back to the first position to continue its cyclic switching motion at a time interval ratio of $T_1/T_2$. First and second deposit patterns 64, 66 form an overlapped region 68, having a density $D_1+D_2$, and a length which substantially corresponds to distance $L_x$ between first and second nozzle members 26, 28. As a result, absorbent particles are deposited in a discrete area 70 of a length $L_z$ positioned in a middle section of each individual pad unit 60 to leave front and rear sections which are substantially free of absorbent particles. The discrete area 70 of absorbent particles further consists of three discrete zones of at least two different particle concentrations or densities $D_1$, $D_1+D_2$ and $D_2$. When the particle discharge rates and intervals from first and second nozzle members 26, 28 are equally adjusted, $D_1$ is approximately equal to $D_2$, and thus the particle density of the central zone is twice as much as that of the front and rear zones in the discrete area 70 of absorbent particles.

As will be appreciated from the foregoing description, a resultant pattern of absorbent particles in fluff layer 12 is primarily determined by time intervals $T_1$ and $T_2$, the time interval ratio $T_1/T_2$, and the distance $L_x$ between the first and second nozzle members 26, 28. The other parameters, such as a conveying speed of conveyer means 24 and the particle discharge rate from the nozzle means 22, may be substantially constant at their desired values associated with product specifications. Specifically, the first and second nozzle members 26, 28 may be conveniently set to provide substantially equal particle discharge pulses therefrom. Time intervals $T_1$ and $T_2$ control the lengths $L_1$, $L_2$ of first and second deposit patterns 64, 66, with the time interval ratio $T_1/T_2$ controlling the discrete patterning of absorbent particles in fluff layer 12 to achieve the desired particle distribution. Notably, the time interval ratio $T_1/T_2$ determines the position of overlapped region 68 in discrete area 70 of absorbent particles. Distance $L_x$ between the first and second nozzle members 26, 28 determines and corresponds to the maximum possible length of overlapped region 68 of first and second deposit patterns of absorbent particles. As will be appreciated, if $L_x$ is equal to zero, then there will be a continuous deposit of absorbent particles in the fluff layer. Accordingly, the first and second nozzle members 26, 28 may be arranged to be longitudinally adjustable.

In the particular embodiment where time interval ratio is set to 1 to 1, time intervals $T_1$, $T_2$ are set to such values that lengths $L_1$, $L_2$ of absorbent particle deposit are each equal to one half of individual pad length $L_t$. This results in distance $L_x$ being one quarter of the individual pad length $L_t$ thereby creating four separate and distinct absorbent particle density zones respectively having one quarter of the length of pad unit length $L_t$, as illustrated in FIG. 6 (designated Zones 1 to 4).

In another particular embodiment where time interval ratio $T_1/T_2$ is set to ⅓, the nozzle means can provide a first deposit of absorbent particles having a length equal to distance $L_x$ during time interval $T_1$, with the overlapped region 68 positioned at a front one third zone of discrete area 70 of absorbent particles. Therefore, suitable value settings of time interval $T_1$ with respect to distance $L_x$ and time interval $T_1/T_2$ result in the a desired zoned placement of overlapped region 68 in discrete area 70 of absorbent particles. As will be appreciated, appropriate adjustment permits the present apparatus to be operated so that overlapped regions of absorbent particles can be positioned as desired along the length of each individual absorbent pad unit.

In a further embodiment of the present invention, the second nozzle 28 is not used, and a recirculation pipe 74 is joined in communication via a junction 72, with the second outlet port 44 of the valve means 30. This arrangements acts to periodically direct the gas-entrained stream of absorbent particles from valve means 30 back to particle supply means 14 through the recirculation pipe 74. A cyclone separator (not shown) or like device may be employed to separate the absorbent particles 10 from the entraining gas and introduce them back into particle supply means. During a time interval $T_2$, valve means 30 is positioned for recirculating absorbent particles back into particle supply means 14, and no absorbent particles are deposited in fluff pulp 12 being conveyed. This further allows formation of a zone which contains substantially no absorbent particles. The relationship between the leading edge of discrete area 70 and the leading edge of individual pad unit 60, or cut line 62, can be suitably adjusted by selecting time intervals $T_1$, $T_2$ and time interval ratio $T_1/T_2$, for achieving the desired pattern and positioning of absorbent particle disposition.

While first and second nozzle members 26, 28 are illustrated in the foregoing embodiment as being aligned with each other in the direction of movement X of fibrous material 12, they may be laterally offset with respect to a lateral centerline of continuous fibrous material. Such offset would alter the width of the overlapped region 68 of discrete area 70 in proportion thereto. To this end, first and second nozzle members 26, 28 may be arranged to be laterally adjustable.

Absorbent particles 10 may be any type of absorbent material in a particle form. Suitable absorbent material includes absorbent fibers, superabsorbent polymers, absorbent fiber/polymer composites, or any equivalent or combination thereof.

Fibrous material 12 preferably comprises cellulosic fibers such as wood pulp fibers, cotton linters, and the like. Other cellulosic fibers that might be used are rayon fibers, flax, jute and the like. Alternatively, hydrophilic synthetic fibers may be used. Such synthetic fibers include polyethylene, polypropylene, nylon, polyester and the like.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover by the appended claims all such modifications as fall within the scope of the claims.

What is claimed is:

1. An apparatus for zoned application of particles in fibrous material, comprising:
   conveyer means for moving said fibrous material in one direction;
   conduit means connected to a supplier for supplying a gas-entrained stream of said particles;
   nozzle means connected to said conduit means for discharging said gas-entrained particles to said fibrous material, said nozzle means comprising first and second nozzle members spaced from each other in at least said one direction of movement of said fibrous material;
   valve means for regulating communication between said conduit means and said nozzle means, said valve means being switchable between a first position wherein said gas-entrained particles are directed to said first nozzle member and a second position wherein said gas-entrained particles are directed to said second nozzle member; and
   control means for controlling said valve means so as to cause said valve means to switch between said first and second positions whereby different concentration zones of said particles are formed on said fibrous material.

2. The apparatus of claim 1, wherein said first and second nozzle members are aligned with each other along said one direction.

3. The apparatus of claim 1, wherein said spacing between the first and second nozzle members is adjustable in at least said one direction.

4. The apparatus of claim 1, wherein said valve means comprises a valve body defining an inlet port and first and second outlet ports, and a valve member movable within said valve body to alternately join said inlet port in communication with said first and second outlet ports.

5. The apparatus of claim 1, wherein said control means is an electromechanical actuator for controlling said valve means to cycle between said first and second valve positions.

6. The apparatus of claim 5, wherein said control means include programmable limit switch means.

7. A method for zoned application of particles in fibrous material, comprising:
   moving said fibrous material in one direction;
   supplying a gas-entrained stream of said particles through conduit means;
   providing nozzle means connected to said conduit means for discharging said gas-entrained particles into said fibrous material, said nozzle means comprising first and second nozzle members;
   spacing said first and second nozzle members from each other in at least said one direction;
   providing valve means for regulating communication between said conduit means and said nozzle means, said valve means being switchable between a first position wherein said gas-entrained particles are directed to said first nozzle member and a second position wherein said gas-entrained particles are directed to said second nozzle member, and
   controlling said valve means to switch between said first and second positions to form a first deposit of particles from said first nozzle member and a second deposit of particles from said second nozzle member to form different concentration zones of said particles on said fibrous material.

8. The method of claim 7, wherein
in said controlling step, said first deposit and said second deposit are formed to have respective lengths in said one direction at a ratio of 1 to 1.

9. The method of claim 7, wherein
said spacing step comprises positioning said second nozzle member downstream of said first nozzle member in said one direction, and
said controlling step comprises controlling said valve means to switch from the first position to the second position on or after a leading edge of a first deposit region of the particles being discharged by said first nozzle member reaches an area onto which said particles are discharged by said second nozzle member, and then to switch from the second position to the first position on or after a trailing edge of said first deposit region reaches said area to form a second deposit region of the particles being discharged by said second nozzle member, said first and second deposit regions forming an overlapped region.

10. The method of claim 7, including
positioning said second nozzle member downstream of and in alignment with said first nozzle member along said one direction.

11. The method of claim 7, wherein
said fibrous material is a plurality of absorbent pads, and said moving step comprises moving said absorbent pads in end-to-end relationship, and said spacing step includes positioning said second nozzle member downstream of said first nozzle member by a distance that is from about a quarter to about a half of a length of one of said absorbent pads.

12. The method of claim 11, wherein
in said spacing step said distance is set to a quarter of a length of one of said absorbent pads, and in said controlling step said first deposit and said second deposit are formed to have respective lengths in said one direction at a ratio of 1 to 1.

13. An apparatus for depositing superabsorbent particles in fibrous material, comprising:
conveying means for conveying said fibrous material;
means for supplying an air-entrained stream of said superabsorbent particles;
nozzle means positioned in relation to said conveying means for dispensing said particles into said fibrous material; and
valve means for joining said supply means in communication with said nozzle means, said valve means comprising a valve body defining an inlet port, and first and second outlet ports, and a valve member movably mounted in said valve body for alternately joining said inlet port in communication with said outlet ports,
said valve body defining a valve chamber defined by a pair of diverging side walls respectively extending from said inlet port to said outlet ports and forming a bifurcated flow passage,
said valve member comprising a wedge-shaped vane movably mounted intermediate said outlet ports for alternately joining said outlet ports with said inlet port, said wedge-shaped vane having a tapered configuration defining an apex extending into said bifurcated flow passage, said valve member being pivotally movable so that opposite side surfaces thereof respectively move against said diverging side walls of said valve body as said valve member moves between first and second positions thereof for alternately joining said inlet port in communication with said first and second outlet ports, said valve member defining with said valve body first and second flow passages attendant to positioning of said valve member in said first and second positions thereof, with each of said first and second flow passages having a cross-sectional area substantially equal to the cross-sectional area of said inlet port and the respectively associated one of said first and second outlet ports.

14. The apparatus of claim 13, wherein
said nozzle means comprises first and second nozzle members respectively joined in communication with said first and second outlet ports.

15. The apparatus of claim 13, wherein
said nozzle means comprises a nozzle member joined in communication with said first outlet port, said apparatus comprising recirculation means joining said second outlet port in communication with said supply means.

16. An apparatus for depositing superabsorbent particles in fibrous material, comprising:
conveying means for conveying said fibrous material;
means for supplying an air-entrained stream of said superabsorbent particles;
nozzle means positioned in relation to said conveying means for dispensing said particles into said fibrous material; and
valve means for joining said supply means in communication with said nozzle means, said valve means comprising a valve body defining an inlet port, and first and second outlet ports, and a valve member movably mounted in said valve body for alternately joining said inlet port in communication with said outlet ports; and
means for augmenting flow of said stream of superabsorbent particles, comprising means for introducing pressurized air in at least one of said inlet and outlet ports,
said flow augmenting means comprising a plurality of angled inlets joined to annular passage means positioned at said one of said inlet and outlet ports, said angled inlets extending to said one of said inlet and outlet ports.

17. A method for zoned application of particles in fibrous material, comprising:
moving said fibrous material in one direction;
supplying a gas-entrained stream of said particles through conduit means;
providing nozzle means connected to said conduit means for discharging said gas-entrained particles into said fibrous material, said nozzle means comprising first and second nozzle members;
spacing said first and second nozzle members from each other in at least said one direction, including positioning said second nozzle member downstream of said first nozzle member in said one direction;
providing valve means for controlling flow of said gas-entrained particles from said conduit means to each of said first and second nozzle members of said nozzle means, said valve means being operable to alternately direct gas-entrained particles to said first nozzle member and to said second nozzle member, and controlling said valve means to switch between directing the gas-entrained particles to said first nozzle member to form a first deposit region of the particles and the second nozzle member to form a second deposit region of the particle to form different concentration zones of said particles on said fibrous material.

18. The method of claim 17, wherein said controlling step comprises controlling said valve means to switch from the first nozzle member to the second nozzle member on or after a leading edge of the first deposit region of the particles being discharged by said first nozzle member reaches an area onto which said particles are discharged by said second nozzle member, and then to switch from the second nozzle member to the first nozzle member on or after a trailing edge of said first deposit region reaches said area to form the second deposit region of the particles being discharged by said second nozzle member, said first and second deposit regions forming an overlapped region.

19. The method of claim 17, wherein said fibrous material is a plurality of absorbent pads, and said moving step comprises moving said absorbent pads in end-to-end relationship, and said spacing step includes positioning said second nozzle member downstream of said first nozzle member by a distance that is from about a quarter to about a half of a length of one of said absorbent pads.

* * * * *